(12) United States Patent
Plehn

(10) Patent No.: US 9,591,824 B1
(45) Date of Patent: Mar. 14, 2017

(54) INBRED CORN LINE IAA13BM

(71) Applicant: Agrigenetics, Inc., Indianapolis, IN (US)

(72) Inventor: Steve J. Plehn, Juneau, WI (US)

(73) Assignee: Agrigenetics Inc., Indianapolis, IN (US)

( * ) Notice: Subject to any disclaimer, the term of this patent is extended or adjusted under 35 U.S.C. 154(b) by 0 days.

(21) Appl. No.: 14/735,597

(22) Filed: Jun. 10, 2015

Related U.S. Application Data

(60) Provisional application No. 62/016,940, filed on Jun. 25, 2014.

(51) Int. Cl.
*C12N 15/82* (2006.01)
*A01H 5/00* (2006.01)
*A01H 5/10* (2006.01)
*A01H 1/02* (2006.01)
*C12N 5/04* (2006.01)

(52) U.S. Cl.
CPC .............. *A01H 5/10* (2013.01); *A01H 1/02* (2013.01); *C12N 5/04* (2013.01)

(58) Field of Classification Search
CPC ........................................................ A01H 5/10
USPC ..................................................... 800/320.1
See application file for complete search history.

(56) References Cited

U.S. PATENT DOCUMENTS

| | | | |
|---|---|---|---|
| 5,523,520 A | 6/1996 | Hunsperger et al. | |
| 6,025,547 A | 2/2000 | Stucker | |
| 6,096,953 A | 8/2000 | Hoffbeck | |
| 7,476,785 B1 * | 1/2009 | Getschman | A01H 5/10 435/412 |

OTHER PUBLICATIONS

Allard, In Principles of Plant Breeding, John Wiley & Sons, Inc. pp. 155-156, 1960.
Phillips, et al., In Corn and Corn Improvement, ASA Monograph No. 18, 3rd edition, pp. 345,358, 1988.
Eshed, et al., Genetics (1996), vol. 143, pp. 1807-1817.
Kraft, et al., Theoretical Applied Genetics (2000), vol. 101, pp. 323-326.
Murray, et al., Proceedings of the 43rd Annual Corn and Sorghum Industry Research Conference, vol. 43, p. 72-87, 1988.

\* cited by examiner

*Primary Examiner* — Li Zheng
(74) *Attorney, Agent, or Firm* — Eric J. Kraus

(57) ABSTRACT

An inbred corn line, designated IAA13BM, the plants and seeds of the inbred corn line IAA13BM, methods for producing a corn plant, either inbred or hybrid, produced by crossing the inbred corn line IAA13BM with itself or with another corn plant, and hybrid corn seeds and plants produced by crossing the inbred line IAA13BM with another corn line or plant and to methods for producing a corn plant containing in its genetic material one or more transgenes and to the transgenic corn plants produced by that method. This invention also relates to inbred corn lines derived from inbred corn line IAA13BM, to methods for producing other inbred corn lines derived from inbred corn line IAA13BM and to the inbred corn lines derived by the use of those methods.

25 Claims, No Drawings

US 9,591,824 B1

INBRED CORN LINE IAA13BM

This application claims a priority based on provisional application 62/015,636 which was filed in the U.S. Patent and Trademark Office on Jun. 23, 2014, the entire disclosure of which is hereby incorporated by reference.

FIELD OF THE INVENTION

This invention is in the field of corn breeding. In particular, the invention relates to an inbred corn line designated IAA13BM that includes plants and seeds of inbred corn line IAA13BM. Methods for producing corn plants, such as inbred corn plants, hybrid corn plants, or other corn plants, as by crossing inbred corn line IAA13BM with itself or any different corn plant are an integral part of this invention as are the resultant corn plants including the plant parts and seeds. This invention further relates to methods for producing IAA13BM-derived corn plants, to methods for producing male sterile IAA13BM corn plants and to methods for regenerating such plants from tissue cultures of regenerable cells as well as the plants obtained therefrom. Methods for producing a corn plant containing in its genetic material one or more transgenes and to the transgenic corn plants produced by that method are also a part of this invention.

BACKGROUND OF THE INVENTION

Corn (*Zea mays* L.) is the most important and abundant crop produced in the United States. Corn is used as human food, livestock feed, and as raw material in industry. The food uses of corn include kernels for human consumption, dry milling products such as grits, meal and flour, and wet milling products such as corn starch, corn syrups, and dextrose. Corn oil recovered from corn germ is a by-product of both dry and wet milling industries. Both grain and non-grain portions of corn plants are used extensively as livestock feed, primarily for beef cattle, dairy cattle, hogs, and poultry.

Corn is used to produce ethanol while corn starch and flour are used in the paper and textile industries. Corn is also used in adhesives, building materials, foundry binders, laundry starches, explosives, oil-well muds, and other mining applications. Plant parts other than the grain of corn are also used in industry; for example, stalks and husks are made into paper and wallboard and cobs are used for fuel and to make charcoal.

The goal of a corn breeder is to improve a corn plant's performance and therefore, its economic value by combining various desirable traits into a single plant. Improved performance is manifested in many ways. Higher yields of corn plants contribute to a more abundant food supply, a more profitable agriculture and a lower cost of food products for the consumer. Improved quality makes corn kernels more nutritious. Improved plant health increases the yield and quality of the plant and reduces the need for application of protective chemicals. Adapting corn plants to a wider range of production areas achieves improved yield and vegetative growth Improved plant uniformity enhances the farmer's ability to mechanically harvest corn.

Corn is a monoecious plant, i.e., corn has imperfect flowers—male, pollen-producing flowers and separate female, pollen receiving flowers on the same plant. The male flowers are located at the top of the plant in the tassel, and the female flowers are located about midway up the stalk in the ear shoot. Each male flower has three anthers and each female flower includes a husk that envelops the cob and silks that emerge from the end of the cob and husks. Pollination is consummated by transfer of pollen from the tassels of the male flower to the silks of the female flowers.

Because corn has separate male and female flowers, corn breeding techniques take advantage of the plant's ability to be bred by both self-pollination and cross-pollination. Self-pollination occurs when pollen from the male flower is transferred to a female flower on the same plant. Cross-pollination occurs when pollen from the male flower is transferred to a female flower on a different plant.

A plant is sib-pollinated (a type of cross-pollination) when individuals within the same family or line are used for pollination (i.e. pollen from a family member plant is transferred to the silks of another family member plant). Self-pollination and sib-pollination techniques are traditional forms of inbreeding used to develop new inbred corn lines but other techniques exist to accomplish inbreeding. New inbred corn lines are developed by inbreeding heterozygous plants and practicing selection for superior plants for several generations until substantially homozygous plants are obtained. During the inbreeding process with corn, the vigor of the lines decreases and after a sufficient amount of inbreeding, additional inbreeding merely serves to increase seed of the developed inbred. Inbred corn lines are typically developed for use in the production of hybrid corn lines.

Natural, or open pollination, occurs in corn when wind blows pollen from the tassels to the silks that protrude from the tops of the ear shoot and may include both self- and cross-pollination. Vigor is restored when two different inbred lines are cross-pollinated to produce the first generation ($F_1$) progeny. A cross between two defined homozygous inbred corn plants always produces a uniform population of heterozygous hybrid corn plants and such hybrid corn plants are capable of being generated indefinitely from the corresponding inbred seed supply.

When two different, unrelated inbred corn parent plants are crossed to produce an $F_1$ hybrid, one inbred parent is designated as the male, or pollen parent, and the other inbred parent is designated as the female, or seed parent. Because corn plants are monoecious, hybrid seed production requires elimination or inactivation of pollen produced by the female parent to render the female parent plant male sterile. This serves to prevent the inbred corn plant designated as the female from self-pollinating. Different options exist for controlling male fertility in corn plants such as manual or mechanical emasculation (or detasseling), genetic male sterility, and application of gametocides. Incomplete removal or inactivation of the pollen in the female parent plant provides the potential for inbreeding which results in the unwanted production of self-pollinated or sib-pollinated seed. Typically, this seed is unintentionally harvested and packaged with hybrid seed.

The development of new inbred corn plants and hybrid corn plants is a slow, costly interrelated process that requires the expertise of breeders and many other specialists. The development of new hybrid corn varieties in a corn plant breeding program involves numerous steps, including: (1) selection of parent corn plants (germplasm) for initial breeding crosses; (2) inbreeding of the selected plants from the breeding crosses for several generations to produce a series of inbred lines, which individually breed true and are highly uniform; and, (3) crossing a selected inbred line with an unrelated line to produce the $F_1$ hybrid progeny having restored vigor.

Inbred corn plants and other sources of corn germplasm are the foundation material for all corn breeding programs.

Despite the existence and availability of numerous inbred corn lines and other source germplasm, a continuing need still exists for the development of improved germplasm because existing inbred parent corn lines lose their commercial competitiveness over time. To protect and to enhance yield production, trait technologies and seed treatment options provide additional crop plan flexibility and cost effective control against insects, weeds and diseases, thereby further enhancing the potential of hybrids with IAA13BM as a parent.

DETAILED DESCRIPTION OF THE INVENTION

I. Definitions of Plant Characteristics

In the description and examples that follow, a number of terms are used. To provide a clear and consistent understanding of the specification and claims, including the scope to be given such terms, the following definitions are provided.

Anther Color: Recorded at the time of pollen shed when anthers are actively dehiscing pollen as a standard color name [Light Green (1), Green-Yellow (5), Pale Yellow (6), Yellow (7), Salmon (9), Pink (11), Cherry Red (13), Purple (17), Tan (22)] and Munsell color code.

Anthocyanin in Brace Roots: Relative rating of the expression of anthocyanin in the brace roots (none, faint, 50% purpling/moderate, and dark) recorded two weeks after flowering.

Biomass: Total amount of above-ground plant material harvested, measured in tons per acre adjusted for 65% moisture.

Cob Color: Recorded as a standard color name [Pink-Orange (10), Pink (11), Light Red (12), Cherry Red (13), Red (14), White (19)] and Munsell color code.

Crude protein: Available and unavailable protein; measured as total nitrogen multiplied by 6.25 and as a percentage of total dry matter.

Ears Per Stalk: Number of ears with seed set on each plant.

Ear Height: Distance measured in centimeters from the ground to the highest placed ear node (attachment point of the ear shank) of the uppermost developed ear on the stalk.

Ear Length: Length of an unhusked ear from the butt to the tip; measured in centimeters.

Ear-Node Leaf Width: Width of the ear-node leaf at its widest point; measured in centimeters.

Ear Taper: Relative taper of the unshelled ear; rated as Slight or nearly straight, Average, or Extreme or conical.

Endosperm Type: Region of the kernel between the germ and the seed coat; rated as sweet, extra sweet (sh2), normal starch, high amylase starch, waxy, high protein, high lysine, supersweet (se), high oil and other-specify.

Environments: Number of different geographic locations where two hybrids are grown together and in the same experiment.

50% Pollen (GDU from Planting): Number of GDUs after planting when 50% of the plants are shedding pollen.

50% Silk (GDU from Planting): Number of GDUs after emergence when 50% of the plants have extruded silk.

GDU (Growing degree units): Number of heat units accumulated over time calculated using the Barger Method, wherein the heat units for each 24-hour period are: [(Max. temp+Min. temp)/2]−50, with 86° F. the highest maximum temperature used and 50° F. the lowest minimum temperature used.

Genotype: Genetic constitution of a plant, plant part, or cell.

Glume Color: Color of the glume after exposure to sunlight and just before extruding anthers; recorded as a standard color name [Light Green (1), Medium Green (2), Dark Green (3), Very Dark Green (4), Green-Yellow (5), Salmon (9), Pink (11), Cherry Red (13), Red (14), Pale Purple (16)] and Munsell color code.

Kernel Row Alignment: Alignment of kernels scored as straight, slightly curved, or spiral as determined by standing the unshelled ear on its base and looking down at the tip.

Kernel Type: Two of the common types for field corn are Flint and Dent; where Flint has mostly hard, glassy endosperm with smooth, hard seed coats, and Dent has soft cores of starch that cause the end of the kernels to collapse or dent during drying.

Lateral Tassel Branches: Number of primary lateral tassel branches that originate from the central spike.

Leaf Angle: Horizontal (less than 30 degrees), Semi-Erect (30 to 60 degrees), Erect (greater than 60 degrees); measured on the upper half of the plant as the angle between a line perpendicular to the stalk and the underside of a leaf at its base.

Leaf Color: Color of the leaf; recorded as standard color name [Light Green (1), Medium Green (2), Dark Green (3), Very Dark Green (4)] and Munsell color code.

Leaves Above Ear: Number of leaves above the ear leaf.

Munsell Color Code: A system that describes colors based on three characteristics: hue, value (lightness), and chroma (color purity).

NDFD (Neutral Detergent Fiber Digestibility): Percentage of neutral detergent fiber that is digestible; determined in vitro by incubating a ground feed sample in live rumen fluid and measuring its disappearance to simulate the amount and rate of digestion that would occur in the rumen.

Number of Kernel Rows: Total number of kernel rows on the ear. If the rows are indistinct, then this value is an average number of kernels located around the circumference of the ear at the mid-point of its length.

Phenotype: Physical or external appearance of a plant or plant part.

Plant Height: Plant height in centimeters from the ground to the tip of the tassel.

Plots: Number of replicated plantings of a single hybrid that are harvested as data points for analyses in the same experiment.

Population: Number of seeds planted on a per acre basis.

Root Lodging: Percentage of corn plants that lean from the vertical axis at an approximate 30° angle or greater just before anthesis.

Silage moisture: Percentage moisture content of biomass measured at harvest.

Silk Color: Color of the silk three days after its emergence; recorded as standard color name [Light Green (1), Green-Yellow (5), Pale Yellow (6), Yellow (7), Salmon (9), Pink-Orange (10), Pink (11), Cherry Red (13), Purple (17), Tan (22)] and Munsell color code.

Standard Color Names: Color names include Light Green (1), Medium Green (2), Dark Green (3), Very Dark Green (4), Green-Yellow (5), Pale Yellow (6), Yellow (7), Yellow-Orange (8), Salmon (9), Pink-Orange (10), Pink (11), Light Red (12), Cherry Red (13), Red (14), Red and White (15), Pale Purple (16), Purple (17), Colorless (18), White (19), White Capped (20), Buff (21), Tan (22), Brown (23), Bronze (24), Variegated (25), and Other (26).

Starch: Amount of starch carbohydrates; measured by near-infrared (NIR) spectroscopy as a percentage of dry silage matter.

Tillers: Branches that develop from axillary buds at the base of a corn plant; they are morphologically identical to the main stalk and capable of forming their own root system, nodes, internodes, leaves, ears, and tassels. Recorded as present or absent.

Total tract dry matter degradability (TDMD): A compilation of all fiber fractions along the whole tract of the dairy animal; measured as sum of ruminal in situ and post-ruminal in vitro degradabilities as a percentage of dry matter.

II. Inbred Corn Line IAA13BM

A. Inbred Corn Plant IAA13BM

In accordance with one aspect of the present invention, provided is a new yellow dent inbred corn seed and plants thereof designated IAA13BM. The present invention further relates to a method for producing inbred corn seeds that includes, but is not limited to, the steps of planting seed of inbred corn IAA13BM in proximity to itself or to different seed from a same family or line, growing the resulting corn plants under self-pollinating or sib-pollinating conditions with adequate isolation, and harvesting resultant seed obtained from such inbred plants using techniques standard in the agricultural arts such as would be necessary to bulk-up seed such as for hybrid production. The present invention also relates to inbred seed produced by such a method.

In any cross between inbred corn plant IAA13BM and another inbred corn plant, IAA13BM may be designated as the male (pollen parent) or the female (seed parent). Optionally, the seed of inbred corn line IAA13BM may be pretreated to increase resistance of the seed and/or seedlings to stressed conditions, and further, the corn plants or surrounding soil may be treated with one or more agricultural chemicals before harvest. Such agricultural chemicals may include herbicides, insecticides, pesticides and the like. The present invention also relates to a corn plant that expresses substantially all of the physiological and morphological characteristics of inbred corn plant IAA13BM and to a substantially homogenous population of corn plants having all the physiological and morphological characteristics of inbred corn plant IAA13BM. Any corn plants produced from inbred corn plant IAA13BM are contemplated by the present invention and are, therefore, within the scope of this invention. A description of physiological and morphological characteristics of corn plant IAA13BM is presented in Table 1.

TABLE 1

Physiological and Morphological Characteristics of IAA13BM

| Characteristic | Value |
|---|---|
| STALK | |
| Plant Height (cm) | 193 |
| Anthocyanin in Brace Roots (None, Light, Moderate, Dark) | Faint |
| Tillers (Present, Absent) | Yes |
| LEAF | |
| Leaf Angle (Horizontal, Semi-Erect, Erect) | Erect |
| Leaf Color (standard) | Medium Green (2) |
| Leaves Above Ear (count) | 7 |
| Ear-Node Leaf Width (cm) | 10 |

TABLE 1-continued

Physiological and Morphological Characteristics of IAA13BM

| Characteristic | Value |
|---|---|
| TASSEL | |
| 50% Pollen (GDU from Planting) | 1466 |
| Lateral Tassel Branches (count) | 9 |
| Anther Color (standard) | Tan (22) |
| Glume Color (standard) | Tan (22) |
| EAR | |
| 50% Silk (GDU from Planting) | 1523 |
| Silk Color (standard) | Salmon (9) |
| Ears Per Stalk (count) | 2 |
| Ear Length (cm) | 16 |
| Number of Kernel Rows (count) | 16 |
| Kernel-Row Alignment (Straight, Slightly Curved, Spiral) | Straight |
| Ear Taper (Slight, Average, Extreme) | Average |
| Cob Color (standard) | Red (14) |
| KERNEL | |
| Type (Flint, Dent) | Dent |
| Endosperm Type (description) | Normal Starch (3) |

It should be appreciated by one having ordinary skill in the art that, for the quantitative characteristics identified in Table 1, the values presented are typical values. These values may vary due to the environment and accordingly, other values that are substantially equivalent are also within the scope of the invention.

Inbred corn line IAA13BM shows uniformity and stability within the limits of environmental influence for the traits described in Table 1. Inbred IAA13BM has been self-pollinated and ear-rowed a sufficient number of generations with careful attention paid to uniformity of plant type to ensure the homozygosity and phenotypic stability necessary to use in large scale, commercial production. The line has been increased both by hand and sib-pollinated in isolated fields with continued observations for uniformity. No variant traits have been observed or are expected in IAA13BM.

The present invention also relates to one or more corn plant parts of inbred corn plant IAA13BM. Corn plant parts include plant cells, plant protoplasts, plant cell tissue cultures from which corn plants can be regenerated, intact genomic plant DNA, plant calli, plant clumps, and plant cells that are intact in plants or parts of plants, such as embryos, pollen, ovules, flowers, seeds, kernels, ears, cobs, leaves, husks, stalks, roots, root tips, brace roots, lateral tassel branches, anthers, tassels, glumes, silks, tillers, and the like.

B. Inbred Corn Seed Designated IAA13BM

A corn kernel is composed of four structural parts: (1) the pericarp, which is a protective outer covering (also known as bran or hull); (2) the germ (also known as an embryo); (3) the endosperm; and, (4) the tip cap, which is the point of attachment to the cob. Another aspect of the present invention is one or more parts of inbred corn seed IAA13BM, such as the pericarp of inbred corn seed IAA13BM or the germ and/or the endosperm of inbred corn seed IAA13BM which remain upon removal of the pericarp and adhering remnants of the seed coat.

Inbred corn seed designated IAA13BM may be provided as a substantially homogenous composition of inbred corn seed designated IAA13BM, that is, a composition that consists essentially of inbred corn seed IAA13BM. Such a substantially homogenous composition of inbred corn seed IAA13BM is substantially free from significant numbers of other inbred and/or hybrid seed so that the inbred seed forms from about 90% to about 100% of the total seed. Preferably, a substantially homogenous composition of the inbred corn seed contains from about 98.5%, 99%, or 99.5% to about 100% of the inbred seed, as measured by seed grow outs. The substantially homogenous composition of inbred corn seed of the invention may be separately grown to provide substantially homogenous populations of inbred corn plants. However, even if a population of inbred corn plants is present in a field with other different corn plants, such as in a commercial seed-production field of single-cross hybrid corn planted in a ratio of 1 male pollinator row to 4 female seed-parent rows, such a population would still be considered to be within the scope of the present invention.

Corn yield is affected by the conditions to which seeds and seedlings (young plants grown from seeds) are exposed. Seeds and seedlings may be exposed to one of, or a combination of, for example, cold, drought, salt, heat, pollutants, and disease, all of which are conditions that potentially retard or prevent the growth of crops therefrom. For example, temperature extremes are typical in the upper Midwest region of the United States. Furthermore, diseases evolved from pathogens and deterioration caused by fungi are potentially harmful to seeds and seedlings. Thus, it is desirable to treat seeds as by coating or impregnating the seeds with compositions that render the seeds and seedlings grown therefrom more hardy when exposed to such adverse conditions.

Accordingly, another aspect of the present invention relates to a coated and/or impregnated seed or corn inbred line designated IAA13BM and to coated and/or impregnated seed derived therefrom. Various agents have been used to treat seeds to increase resistance of the plants to stressed conditions, such as cold, drought, salt, and fungi. Such agents include, for example, sodium methylphenyl-pentadienate, trichloroacetic acid, polyoxyalkylene-organo-siloxane block copolymer, 5-aminolevulinic acid, salicylic acid, thiamethoxam, potassium chloride, and polyvinyl alcohol and are useful alone, or in combination in the present invention.

When pre-treating seeds according to the present invention such as before the seeds are planted, the seeds are contacted with the composition of interest, as by coating seeds, spraying seeds, and soaking seeds or a combination thereof, by methods well known to those skilled in the art.

C. Deposit Information

Applicants have made a deposit of at least 2,500 seeds of inbred corn plant IAA13BM with the American Type Culture Collection (ATCC), 10801 University Boulevard, Manassas, Va. 20110 USA, under ATCC Accession No. PTA-122499. The seeds deposited with the ATCC on Sep. 4, 2015, were taken from a deposit maintained by Agrigenetics, Inc. d/b/a Mycogen Seeds since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will maintain and will make this deposit available to the public pursuant to the Budapest Treaty.

III. Processes of Preparing Novel Corn Plants

A. Novel Inbred Corn Plants Obtained from Inbred IAA13BM

Various breeding schemes may be used to produce new inbred corn lines from IAA13BM. In one method, generally referred to as the pedigree method, IAA13BM may be crossed with another different corn plant such as a second inbred parent corn plant, which either itself exhibits one or more selected desirable characteristic(s) or imparts selected desirable characteristic(s) to a hybrid combination. Examples of potentially desired characteristics include greater yield, better stalks, better roots, reduced time to crop maturity, better agronomic quality, higher nutritional value, higher starch extractability or starch fermentability, resistance and/or tolerance to insecticides, herbicides, pests, heat and drought, and disease, and uniformity in germination times, stand establishment, growth rate, maturity and kernel size. If the two original parents corn plants do not provide all the desired characteristics, then other sources can be included in the breeding population. Elite inbred lines, that is, pure breeding, homozygous inbred lines, can also be used as starting materials for breeding or source populations from which to develop inbred lines.

Thereafter, resulting seed is harvested and resulting superior progeny plants are selected and selfed or sib-mated in succeeding generations, such as for about 5 to about 7 or more generations, until a generation is produced that no longer segregates for substantially all factors for which the inbred parents differ, thereby providing a large number of distinct, pure-breeding inbred lines.

In another embodiment for generating new inbred corn plants, generally referred to as backcrossing, one or more desired traits may be introduced into inbred parent corn plant IAA13BM (the recurrent parent) by crossing the IAA13BM plants with another corn plant (referred to as the donor or non-recurrent parent) which carries the gene(s) encoding the particular trait(s) of interest to produce $F_1$ progeny plants. Both dominant and recessive alleles may be transferred by backcrossing. The donor plant may also be an inbred, but in the broadest sense can be a member of any plant variety or population cross-fertile with the recurrent parent. Next, $F_1$ progeny plants that have the desired trait are selected. Then, the selected progeny plants are crossed with IAA13BM to produce backcross progeny plants. Thereafter, backcross progeny plants comprising the desired trait and the physiological and morphological characteristics of corn inbred line IAA13BM are selected. This cycle is repeated for about one to about eight cycles, preferably for about 3 or more times in succession to produce selected higher backcross progeny plants that comprise the desired trait and all of the physiological and morphological characteristics of corn inbred line IAA13BM listed in Table 1 as determined at the 5% significance level when grown in the same environmental conditions. Exemplary desired trait(s) include insect resistance, cytoplasmic male sterility, enhanced nutritional quality, waxy starch, herbicide resistance, yield stability, yield enhancement and resistance to bacterial, fungal and viral disease. One of ordinary skill in the art of plant breeding would appreciate that a breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987) which is incorporated herein by reference. Mean trait values may be used to determine whether trait differences are significant, and preferably the traits are measured on plants grown under the same environmental conditions.

This method results in the generation of inbred corn plants with substantially all of the desired morphological and physiological characteristics of the recurrent parent and the particular transferred trait(s) of interest. Because such inbred corn plants are heterozygous for loci controlling the transferred trait(s) of interest, the last backcross generation would subsequently be selfed to provide pure breeding progeny for the transferred trait(s).

Backcrossing may be accelerated by the use of genetic markers such as SSR, RFLP, SNP or AFLP markers to identify plants with the greatest genetic complement from the recurrent parent.

Direct selection may be applied where a single locus acts as a dominant trait, such as the herbicide resistance trait. For this selection process, the progeny of the initial cross are sprayed with the herbicide before the backcrossing. The spraying eliminates any plants which do not have the desired herbicide resistance characteristic, and only those plants which have the herbicide resistance gene are used in the subsequent backcross. In the instance where the characteristic being transferred is a recessive allele, it may be necessary to introduce a test of the progeny to determine if the desired characteristic has been successfully transferred. The process of selection, whether direct or indirect, is then repeated for all additional backcross generations.

It should be appreciated by those having ordinary skill in the art that backcrossing can be combined with pedigree breeding as where inbred IAA13BM is crossed with another corn plant, the resultant progeny are crossed back to inbred IAA13BM and thereafter, the resulting progeny of this single backcross are subsequently inbred to develop new inbred lines. This combination of backcrossing and pedigree breeding is useful as when recovery of fewer than all of the IAA13BM characteristics than would be obtained by a conventional backcross are desired.

In an additional embodiment of the present invention, new inbred corn plants can be developed by a method generally referred to as haploid breeding. In this methodology, haploid plants are generated from diploid, heterozygous corn plants that result from crossing inbred corn plant IAA13BM with another, different corn plant. Such haploid corn plants may be generated by methods known to those skilled in the art such as by culturing haploid anthers or embryos from a diploid plant. Alternately, such haploid corn plant may be generated by crossing the diploid heterozygous corn plant with a corn plant that comprises a haploid inducing gene, such as the mutant gene "indeterminate gametophyte" (ig), which, when present in the female parent results in offspring with a greatly enhanced frequency of haploids of both maternal and paternal origin. Thereafter, homozygous diploid plants are produced by the doubling of a set of chromosomes (1N) from a haploid plant generated by self-pollination such as through use of a doubling agent, such as colchicine, nitrous oxide gas, heat treatment and trifluralin. See, e.g., Wan et al., "Efficient Production of Doubled Haploid Plants Through Colchicine Treatment of Anther-Derived Maize Callus", Theoretical and Applied Genetics, 77:889-892, 1989 and U.S. Patent Application No. 20030005479 the disclosure of which is expressly incorporated herein by reference. The technique of haploid breeding is advantageous because no subsequent inbreeding is required to obtain a homozygous plant from a heterozygous source. Thus, in another aspect of this invention a new inbred corn plant is developed by a method that includes the steps of crossing IAA13BM or a hybrid made with IAA13BM with another inbred corn plant having a propensity to generate haploids to produce haploid progeny plants, and selecting desirable inbred corn plants from the haploid progeny plants.

The present invention also relates to novel corn plants produced by a method generally referred to as mutation breeding whereby one or more new traits may be artificially introduced into inbred line IAA13BM. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis and selected, the trait may then be incorporated into existing germplasm by traditional breeding techniques. Details of mutation breeding can be found in "Principals of Cultivar Development" Fehr, 1993 Macmillan Publishing Company the disclosure of which is incorporated herein by reference.

The mutagenesis treatment may be applied to various stages of plant development, including but not limited to cell cultures, embryos, microspores and shoot apices as well as to corn kernels. By way of example, pollen may be mixed with a solution of 1 ml EMS and 100 mls Fisher paraffin oil (stock diluted by 1 ml and 15 mls oil solution) every minute for the first 5 minutes and then every five minutes for 45 minutes to keep the pollen suspended. Thereafter, the pollen/paraffin oil solution is brushed onto the silks of developing ears. A tassel bag is used to cover the ear to prevent contamination. The ear is picked at maturity and then resultant seeds or the plants therefrom are screened for the desired mutant trait(s).

Once inbred lines are created, the next step is to determine if the inbreds have any value. This is accomplished by techniques of measuring the combining ability of the new inbred plant, as well as the performance of the line itself. Combining ability refers to a line's contribution as a parent when crossed with other lines to form hybrids. Specific combining ability (SCA) refers to the ability of a line to cross to another specific inbred to form a hybrid. General combining ability (GCA) refers to the ability of a line to cross to a wide range of lines to form hybrids. The methodology of forming hybrids to evaluate an inbred line's contribution as a parent for the purpose of selecting superior lines is interchangeably known as experimental, top or test crossing.

B. Novel Inbred Plants Obtained from a Hybrid Having Inbred IAA13BM as a Parent

In accordance with processes of the present invention, a hybrid plant having inbred IAA13BM as a parent is crossed with itself or any different corn plant such as an inbred corn plant or a hybrid corn plant to develop a novel inbred line. For example, a hybrid corn plant having inbred corn plant IAA13BM as a parent may be inbred, i.e., crossed to itself or sib-pollinated, and the resulting progeny each selfed for about 5 to about 7 or more generations, thereby providing a set of distinct, pure-breeding inbred lines wherein each of the lines received all of its alleles from the hybrid corn plant having inbred corn plant IAA13BM as a parent. Double haploid methods can also be used to obtain an inbred corn plant that is homozygous at essentially every locus, wherein the inbred corn plant received all of its alleles from the hybrid corn plant having inbred corn plant IAA13BM as a parent. In other embodiments, a hybrid corn plant having inbred corn plant IAA13BM as a parent is crossed with a different corn plant that may include any inbred corn plant that is not inbred corn plant IAA13BM, any hybrid corn plant that does not have IAA13BM as a parent, another germplasm source, a haploid or mutation inducing stock, or a trait donor plant, thereby providing a set of distinct, pure-breeding inbred lines. The resulting inbred lines could then be crossed with other inbred or non-inbred lines and the resulting inbred progeny analyzed for beneficial characteristics. In this way, novel inbred lines conferring desirable characteristics could be identified.

C. "Chasing Selfs"

Both female and male inbred seed may occasionally be found within a commercial bag of hybrid seed. Chasing the selfs involves identifying inbred plants within a stand of corn that has been grown from a bag of hybrid corn seed. Once the seed is planted, the inbred plants may be identified and selected due to their decreased vigor, i.e., by their short stature, narrower leaves, and smaller tassels relative to the hybrid plants that grow from the hybrid seed which predominates in a commercial bag of hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another embodiment of the present invention is directed to a method for producing inbred corn plant IAA13BM comprising: (a) planting a collection of seed, such as a collection of seed comprising seed of a hybrid, one of whose parents is inbred corn plant IAA13BM, the collection also comprising seed of the inbred; (b) growing plants from said collection of seed; (c) identifying inbred parent plants; (d) controlling pollination in a manner which preserves homozygosity of the inbred parent plant; and, (e) harvesting resultant seed. Step (c) may further comprise identifying plants with decreased vigor, i.e., plants that appear less robust than the other plants, or identifying plants that have a genetic profile in accordance with the genetic profile of IAA13BM, such as an SSR genetic profile in accordance with Table 5 herein. Corn plants capable of expressing substantially all of the physiological and morphological characteristics of inbred corn plant IAA13BM include corn plants obtained by chasing selfs from a bag of hybrid seed.

One having skill in the art will recognize that once a breeder has obtained inbred corn plant IAA13BM by chasing selfs from a bag of hybrid seed, the breeder can then produce new inbred plants such as by sib-pollinating, i.e., crossing the inbred corn plant IAA13BM with another inbred corn plant IAA13BM, or by crossing the inbred corn plant IAA13BM with a hybrid corn plant obtained by growing the collection of seed.

IV. Novel Hybrid Plants

A. Novel Hybrid Seeds and Plants

In yet another aspect of the invention, processes are provided for producing corn seeds or plants, which processes generally comprise crossing a first parent corn plant with a second parent corn plant wherein at least one of the first parent corn plant or the second parent corn plant is inbred parent corn plant IAA13BM. In some embodiments of the present invention, the first inbred corn plant is IAA13BM and is a female and in other embodiments the first inbred corn plant is IAA13BM and is a male. These processes may be further exemplified as processes for preparing hybrid corn seed or plants, wherein a first inbred corn plant is crossed with a second corn plant of a different, distinct variety to provide a hybrid that has, as one of its parents, the inbred corn plant variety IAA13BM. In this case, a second inbred variety is selected which confers desirable characteristics when in hybrid combination with the first inbred line. In these processes, crossing will result in the production of seed. The seed production occurs regardless whether the seed is collected.

Any time the inbred corn plant IAA13BM is crossed with another, different corn inbred, a first generation ($F_1$) corn hybrid plant is produced. As such, an $F_1$ hybrid corn plant may be produced by crossing IAA13BM with any second inbred corn plant. Therefore, any $F_1$ hybrid corn plant or corn seed which is produced with IAA13BM as a parent is part of the present invention.

When inbred corn plant IAA13BM is crossed with another inbred plant to yield a hybrid, the original inbred can serve as either the maternal or paternal plant with basically, the same characteristics in the hybrids. Occasionally, maternally inherited characteristics may express differently depending on the decision of which parent to use as the female. However, often one of the parental plants is preferred as the maternal plant because of increased seed yield and preferred production characteristics, such as optimal seed size and quality or ease of tassel removal. Some plants produce tighter ear husks leading to more loss, for example due to rot, or the ear husk may be so tight that the silk cannot completely push out of the tip preventing complete pollination resulting in lower seed yields. There can be delays in silk formation which deleteriously affect timing of the reproductive cycle for a pair of parental inbreds. Seed coat characteristics can be preferable in one plant which may affect shelf life of the hybrid seed product. Pollen can shed better by one plant, thus rendering that plant as the preferred male parent. It is generally preferable to use IAA13BM as the male parent.

In embodiments of the present invention, the first step of "crossing" the first and the second parent corn plants comprises planting, preferably in pollinating proximity, seeds of a first inbred corn plant and a second, distinct inbred corn plant. As discussed herein, the seeds of the first inbred corn plant and/or the second inbred corn plant can be treated with compositions that render the seeds and seedlings grown therefrom more hardy when exposed to adverse conditions.

A further step comprises cultivating or growing the seeds of the first and second parent corn plants into plants that bear flowers. If the parental plants differ in timing of sexual maturity, techniques may be employed to obtain an appropriate nick, i.e., to ensure the availability of pollen from the parent corn plant designated the male during the time at which silks on the parent corn plant designated the female are receptive to the pollen. Methods that may be employed to obtain the desired nick include delaying the flowering of the faster maturing plant, such as, but not limited to delaying the planting of the faster maturing seed, cutting or burning the top leaves of the faster maturing plant (without killing the plant) or speeding up the flowering of the slower maturing plant, such as by covering the slower maturing plant with film designed to speed germination and growth or by cutting the tip of a young ear shoot to expose silk.

In a preferred embodiment, the corn plants are treated with one or more agricultural chemicals as considered appropriate by the grower.

A subsequent step comprises preventing self-pollination or sib-pollination of the plants, i.e., preventing the silks of a plant from being fertilized by any plant of the same variety, including the same plant. This is preferably done in large scale production by controlling the male fertility, e.g., treating the flowers so as to prevent pollen production or alternatively, using as the female parent a male sterile plant of the first or second parent corn plant (i.e., treating or manipulating the flowers so as to prevent pollen production, to produce an emasculated parent corn plant or using as a female, a cytoplasmic male sterile version of the corn plant). This control may also be accomplished in large scale production by physical removal of the tassel from the female plant, either by pulling the tassel by hand, cutting with a rotary cutter, or pulling with a mechanical tassel pulling machine. In small scale production, corn breeder's shoot bags, usually plastic or glassine, applied to cover the ear shoot prior to the extrusion of silks provide effective control of unwanted self-pollination or sib-pollination.

Yet another step comprises allowing cross-pollination to occur between the first and second parent corn plants. When the plants are not in pollinating proximity, this is done by placing a bag, usually paper, over the tassels of the first plant and another shoot bag over the ear shoot, prior to the extrusion of silk, of the incipient ear on the second plant. The bags are left in place usually overnight. Since pollen stops shedding each day and loses viability and new pollen is shed each morning, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels and removed from the first plant. Finally, in one continuous motion, the shoot bag is removed from the silks of the incipient ear on the second plant, and the pollen bag containing the captured pollen is placed over the silks of the incipient ear of the second plant, shaken again to disperse the captured pollen, and left in place covering the developing ear to prevent contamination from any unwanted fresh airborne pollen. In large scale production, crossing is accomplished by isolated open-pollinated crossing fields whereby corn plants of the parent designated as the female, which are controlled for male fertility, are allowed to be pollinated by other plants of a different corn type where such plants are adjacent to the plants designated as the female parent.

A further step comprises harvesting the seeds, near or at maturity, from the ear of the plant that received the pollen. In a particular embodiment, seed is harvested from the female parent plant, and when desired, the harvested seed can be grown to produce a first generation ($F_1$) hybrid corn plant.

Yet another step comprises drying and conditioning the seeds, including the treating, sizing (or grading) of seeds, and packaging for sale to growers for the production of grain or forage. As with inbred seed, it may be desirable to treat hybrid seeds with compositions that render the seeds and seedlings grown therefrom more hardy when exposed to adverse conditions. Mention should be made that resulting hybrid seed is sold to growers for the production of grain and forage and not for breeding or seed production.

Still further, the present invention provides a hybrid corn plant produced by growing the harvested seeds produced on the male-sterile plant as well as grain produced by the hybrid corn plant.

A single cross hybrid is produced when two different inbred parent corn plants are crossed to produce first generation $F_1$ hybrid progeny. Generally, each inbred parent corn plant has a genotype which complements the genotype of the other inbred parent. Typically, the $F_1$ progeny are more vigorous then the respective inbred parent corn plants. This hybrid vigor, or heterosis, is manifested in many polygenic traits, including markedly improved yields and improved stalks, roots, uniformity and insect and disease resistance. It is for this reason that single cross $F_1$ hybrids are generally the most sought after hybrid. A three-way, or modified single-cross hybrid is produced from three inbred lines (or synthetics) where two of the inbred lines are crossed (A×B) and then the resulting $F_1$ hybrid is crossed with the third inbred (A×B)×C, as where a modified female is used in the cross. A modified female provides an advantage of improved seed parent yield whereas a modified male improves pollen flow. A double cross hybrid is produced from four inbred lines crossed in pairs (A×B and C×D), thereby resulting in two $F_1$ hybrids that are crossed again. Double cross hybrids are more common in countries wherein less demand exists for higher yielding single cross hybrids. Synthetic populations or crosses are developed by crossing two or more inbred lines (or hybrids, or germplasm sources) together and then employing one of many possible techniques to random mate the progeny. Random mating the progeny is any process used by plant breeders to make a series of crosses that will create a new germplasm pool from which new breeding lines can be derived. Much of the hybrid vigor exhibited by $F_1$ hybrids is lost in the next generation ($F_2$). Consequently, seed from hybrids are not typically used for planting stock.

The utility of the inbred plant IAA13BM also extends to crosses with species other than the *mays* species, such as *diploperennis, luxurians*, and *perennis*. Commonly, suitable species will be of the family Graminaceae, and especially of the genera *Zea, Tripsacum, Coix, Schleachne, Polytoca, Chionachne*, and *Trilobachne*. Of these, *Zea* and *Tripsacum*, are most preferred. Varieties of the grain sorghum *Sorghum bicolor* (L.) Moench can be crossed with inbred corn line IAA13BM.

B. Physical Description of $F_1$ Hybrids and $F_1$ Hybrid Comparison

As mentioned above, testcross hybrids are progressively eliminated following detailed evaluations of their phenotype, including formal comparisons with other commercially successful hybrids. Research small-plot trials and commercial strip trials are used to compare the phenotypes of hybrids grown in as many environments as possible. They are performed in many environments to assess overall performance of the new hybrids and to select optimum growing conditions. Because the corn is grown in close proximity, differential effects of environmental factors that affect gene expression, such as moisture, temperature, sunlight, and pests, are minimized. For a decision to be made to advance a hybrid, it is not necessary that the hybrid be better than all other hybrids. Rather, significant improvements must be shown in at least some traits that would create value for some applications or markets. Some testcross hybrids are eliminated despite being similarly competitive relative to the current commercial hybrids because of the cost to bring a new hybrid to market requires a new product to be a significant improvement over the existing product offering. Such hybrids may also be licensed to other parties who have a need in their commercial product portfolio.

The present invention provides $F_1$ hybrid corn plants obtained from the corn plant IAA13BM. The performance characteristics of an exemplary hybrid produced using IAA13BM as one inbred parent are set forth in Tables 2 and 3. The results in Table 2 compare hybrid performance of inbred IAA13BM and another elite inbred, when each of these inbreds is crossed to the same tester line. The results in Table 3 shows hybrid performance for the hybrid made with IAA13BM and the tester line compared with selected commercial hybrids including Mycogen F2F797 and Mycogen TMF113.

TABLE 2

Comparison of Corn Inbred IAA13BM to Another Inbred in Hybrids with Common Tester Line

| Characteristic | Tester line A × IAA13BM | Tester line A × Inbred C |
|---|---|---|
| Biomass (tons/ac) | 21.1 | 20.9 |
| Silage Moisture (%) | 65.7 | 65.9 |
| NDFD (%) | 67.1 | 67.9 |
| Starch (%) | 31.5 | 28.9 |
| TDMD (%) | 87.7 | 86.4 |
| Crude Protein (%) | 6.9 | 6.8 |
| Plant Height (cm) | 192.5 | 194.1 |
| Ear Height (cm) | 90.4 | 111.3 |
| Root Lodging (%) | 1.4 | 8.3 |
| Population (plants/ac × 1000) | 32410 | 35260 |
| Environments (count) | 21 | 21 |
| Plots/mean (count) | 21 | 21 |

TABLE 3

Hybrid From IAA13BM Compared With Other Commercial Hybrids

| Characteristic | Tester line A × IAA13BM | Mycogen F2F569 | Mycogen F2F488 |
|---|---|---|---|
| Biomass (tons/ac) | 21.8 | 21.2 | 20.0 |
| Silage Moisture (%) | 62.6 | 61.1 | 59.9 |
| NDFD (%) | 64.8 | 64.5 | 65.2 |
| Starch (%) | 31.8 | 29.8 | 33.0 |
| TDMD (%) | 86.2 | 85.0 | 86.3 |
| Crude Protein (%) | 7.0 | 7.0 | 7.3 |
| Plant Height (cm) | 234.5 | 223.0 | 229.4 |
| Ear Height (cm) | 103.5 | 117.4 | 123.4 |
| Stalk Lodging (%) | 0.0 | 0.6 | 0.4 |
| Root Lodging (%) | 0.1 | 4.4 | 3.1 |
| Population (plants/ac) | 37,580 | 38,410 | 36,630 |
| Environments (count) | 30 | 30 | 29 |
| Plots/mean (count) | 30 | 30 | 29 |

V. Novel IAA13BM-Derived Plants

All plants produced using inbred corn plant IAA13BM as a parent are within the scope of this invention, including plants derived from inbred corn plant IAA13BM. This includes plants essentially derived from inbred IAA13BM with the term "essentially derived variety" having the meaning ascribed to such term in 7 U.S.C. §2104(a)(3) of the Plant Variety Protection Act, which definition is hereby incorporated by reference. This also includes progeny plant and parts thereof with at least one ancestor that is inbred corn plant IAA13BM and more specifically where the pedigree of this progeny includes 1, 2, 3, 4, and/or 5 or cross pollinations to inbred corn plant IAA13BM, or a plant that has IAA13BM as a progenitor. All breeders of ordinary skill in the art maintain pedigree records of their breeding programs. These pedigree records contain a detailed description of the breeding process, including a listing of all parental lines used in the breeding process and information on how such line was used. Thus, a breeder would know if IAA13BM were used in the development of a progeny line, and would also know how many breeding crosses to a line other than IAA13BM were made in the development of any progeny line. A progeny line so developed may then be used in crosses with other, different, corn inbreds to produce first generation $F_1$ corn hybrid seeds and plants with superior characteristics.

Accordingly, another aspect of the present invention is methods for producing an inbred corn line IAA13BM-derived corn plant. This method for producing a IAA13BM-derived corn plant, comprises: (a) crossing inbred corn plant IAA13BM with a second corn plant to yield progeny corn seed; and, (b) growing the progeny corn seed, (under plant growth conditions), to yield the IAA13BM-derived corn plant. Such methods may further comprise the steps of: (c) crossing the IAA13BM-derived corn plant with itself or another corn plant to yield additional IAA13BM-derived progeny corn seed; (b) growing the progeny corn seed of step (d) (under plant growing conditions), to yield additional IAA13BM-derived corn plants; and (e) repeating the crossing and growing steps of (c) and (d) from 0 to 7 times to generate further IAA13BM-derived corn plants. Still further, this may comprise utilizing methods of haploid breeding and plant tissue culture methods to derive progeny of the IAA13BM-derived corn plant.

VI. Tissue Cultures and In Vitro Regeneration of Corn Plants

As is well known in this art, tissue culture of corn may be used for the in vitro regeneration of a corn plant. Accordingly, a further aspect of the invention relates to tissue cultures of the inbred corn plant designated IAA13BM, to tissue cultures of hybrid and derived corn plants obtained from IAA13BM, to plants obtained from such tissue cultures and to the use of tissue culture methodology in plant breeding. The term "tissue culture" includes a composition comprising isolated cells of the same type, isolated cells of a different type, or a collection of such cells organized into parts of a plant. Exemplary tissue cultures are protoplasts, calli and plant cells that are intact in plants or parts of plants, such as embryos, pollen, flowers, kernels, ears, cobs, leaves, husks, stalks, roots, root tips, anthers, silk, and the like. In a preferred embodiment, the tissue culture comprises embryos, protoplasts, meristematic cells, pollen, leaves or anthers derived from immature tissues of these plant parts.

A. Immature Embryo Culture

To obtain immature embryos for callus culture initiation, ears are harvested from a corn plant, e.g., an inbred corn plant IAA13BM, a hybrid corn plant having IAA13BM as a parent or a IAA13BM-derived corn plant, approximately 9-10 days post-pollination. Initially, harvested ears are surface sterilized, as by scrubbing with Liqui-Nox® soap, immersion in 70% ethanol for 2-3 minutes, followed by immersion in 20% commercial bleach (0.1% sodium hypochlorite) for about 30 minutes.

Ears are rinsed in sterile, distilled water, and immature zygotic embryos are aseptically excised with the aid of a dissection microscope and cultured on a suitable initiation medium. One having ordinary skill in the art would understand that explants from other tissues, such as immature tassel tissue, intercalary meristems and leaf bases, apical meristems, and immature ears may also be the subject of callus culture initiation. Tissue culture media typically, contain amino acids, salts, sugars, hormones, and vitamins. Most of the media employed to regenerate inbred and hybrid plants have some similar components; the media differ in the composition and proportions of their ingredients depending on the particular application envisioned. Examples of media suitable for culture of plants cells include, but are not limited to an N6 medium, an MS media, or modifications thereof. A preferred media is a 15Ag10 medium (N6 Complete Medium, PhytoTechnology Laboratories C167), 1.0 mg/L 2,4-D, 20 g/L sucrose, 100 mg/L casein hydrolysate (enzymatic digest), 25 mM L-proline, 10 mg/L AgNO$_3$, 2.5 g/L Gelrite, pH 5.8, for about 2-3 weeks with the scutellum facing away from the medium. Tissue showing the proper morphology, Welter, et al., Plant Cell Rep. 14:725-729 (1995), is selectively transferred at biweekly intervals onto fresh 15Ag10 medium for about 6 weeks and then is transferred to "4" medium (N6 Complete Medium Phyto 167), 1.0 mg/L 2,4-D, 20 g/L sucrose, 100 mg/L casein hydrolysate (enzymatic digest), 6 mM L-proline, 2.5 g/L Gelrite, pH 5.8, at bi-weekly intervals for approximately 2 months. Hormones other than an auxin such as 2,4-D may be employed including dicamba, NAA, BAP, 2-NCA, ABA, and picloram. Modifications of these and other basic media may facilitate growth of recipient cells at specific developmental stages.

Regeneration is initiated by transferring callus tissue to a cytokinin-based induction medium, "28" (MS Salts, 30 g/L sucrose, 5 mg/L BAP, 0.025 mg/L 2,4-D at pH of 5.7.) Cells are allowed to grow in low light (13 $\mu EM^{-2}s^{-1}$) for one week then higher light (40 $\mu EM^{-2}s^{-1}$) for about another week. Regeneration of plants is completed by the transfer of mature and germinating embryos to a hormone-free medium, followed by the transfer of developed plantlets to soil and growth to maturity. In a preferred embodiment, the cells are transferred to a hormone-free regeneration medium, "28" lacking plant growth regulators. Thereafter, small (3-5 cm) plantlets are removed and placed into 150×25 mm culture tubes containing SHGA (Schenk and Hilldebrandt salts: 10 g/L sucrose, 1 g/L myo-inositol, 2 g/L Gelrite, pH 5.8) medium.

Once plantlets develop a sufficient root and shoot system, they are transplanted to 4-inch pots containing approximately 0.1 kg of METRO-MIX 360 soil in a growth room or greenhouse. They are grown with a 16-h photoperiod supplemented by a combination of high pressure sodium and metal halide lamps, and are watered as needed with a combination of three different Miracle Grow fertilizer formulations. At the 3-5 leaf stage, plants are transferred to five gallon pots containing approximately 4 kg METRO-MIX 360.

Primary regenerants ($R_1$ plants) are self- or sib-pollinated after an additional 6-10 weeks in five gallon pots, and $R_1$ seed is collected at 40-45 days post-pollination. Alternately, when self- or sib-pollinations are not possible, plants may be outcrossed to elite inbreds.

It will be appreciated by those of ordinary skill in the art that regenerable cultures, including Type I and Type II cultures, may be initiated from immature embryos using other methods, such as those described in, for example, PCT Application WO 95/06128, the disclosure of which is incorporated herein by reference in its entirety.

B. Additional Tissue Cultures and Regeneration

Other means for preparing and maintaining plant tissue cultures are well known in the art. By way of example, a tissue culture comprising organs such as tassels or anthers and pollen (microspores) have been used to produce regenerated plants (U.S. Pat. Nos. 5,322,789 and 5,445,961). Also, meristematic cells (i.e., plant cells capable of continual cell division and characterized by an undifferentiated cytological appearance, normally found at growing points or tissues in plants such as root tips, stem apices, lateral buds, etc.) can be cultured to regenerate fertile plants (U.S. Pat. No. 5,736,369 the disclosure of which is specifically incorporated herein by reference).

VII. Male Sterility

Methods for controlling male fertility in corn plants offer the opportunity for improved plant breeding, particularly for the development of corn hybrids which require the implementation of a male sterility system to prevent the inbred parent plants from self-pollination.

Accordingly, another aspect of the present invention is male-sterile inbred corn plants designated IAA13BM and the production of hybrid corn seed using a male sterility system with such inbred female parent plants that are male sterile. In the event that inbred corn line IAA13BM is employed as the female parent, IAA13BM can be rendered male-sterile by, for example, removing the tassels or "detasseling" IAA13BM parental plants either manually or by machine. By way of example, alternate strips of two corn inbreds may be planted in a field followed by manual or mechanical removal of the pollen-bearing tassels from the designated female inbred. Provided that the female inbreds are sufficiently isolated from foreign corn pollen sources, the ears of the detasseled inbred will be fertilized only from the other male inbred, and the resulting seed will therefore be hybrid seed.

The laborious and occasionally unreliable detasseling process can be minimized by using cytoplasmic male-sterile (CMS) inbreds. Plants of a CMS inbred are male sterile as a result of factors resulting from cytoplasmic as opposed to the nuclear genome. Thus, this characteristic is inherited exclusively through the female parent in corn plants since CMS plants are fertilized with pollen from another inbred that is not male-sterile. Pollen from the second inbred may or may not contribute genes that make the hybrid plants male-fertile. Seed from detasseled fertile corn and CMS produced seed of the same hybrid can be blended to insure that adequate pollen loads are available for fertilization when the hybrid plants are grown. Conventional backcrossing methodology may be used to introgress the CMS trait into inbred IAA13BM.

Alternatively, haploid breeding methods may also be employed to convert inbred IAA13BM to CMS sterility. Haploids are plants which contain only one-half of the chromosome number present in diploid somatic cells, which are cells other than haploid cells such as those found in the germ. There are a few stocks or genetic systems in corn which are known to generate haploids spontaneously. For example, plants are known which possess an indeterminate gametophyte (ig) gene (Kermicle 1969 Science 166:1422-1424) which generate haploids. Additionally, a line known as Stock 6 (See, Birchler, J. A., "Practical Aspects of Haploid Production," The Corn Handbook, Freeling and Walbot (eds). pp. 386-388 (1996)) possesses a propensity to generate haploids. Moreover, RWS (Roeber and Geiger 2001, submitted to Crop Science), KEMS (Deimling, Roeber, and Geiger, 1997, Vortr. Pflanzenzuchtg 38:203-224), or KMS and ZMS (Chalyk, Bylich & Chebotar, 1994, MNL 68:47; Chalyk & Chebotar, 2000, Plant Breeding 119:363-364) also represent inducer lines which be used to produce haploid plants from any genotype. In a preferred aspect of the present invention, cytoplasmic male sterile female plants which possess the ig gene may be used to facilitate the generation of cytoplasmic male sterile inbred versions of IAA13BM of the present invention because the selection of haploids and subsequent doubling permits corn breeders to reach homogeneity more quickly and completely.

Detasseling can also be avoided by the use of chemically induced male sterility in the production of hybrid corn seed. Chemicals that induce male sterility include gametocides, pollen suppressants, and chemical hybridizing agents. The general procedure is to use a foliar spray before flowering, which inhibits production of viable pollen, but does not injure the pistillate reproductive organs or affect seed development. If the treatment is successful and all of the pollen killed, self-pollination will not occur in the treated plants, but the flowers will set seed freely from cross-pollination. In such a case, the parent plants used as the male may either not be treated with the chemical agent or may include a genetic factor which causes resistance to the sterilizing effects of the chemical agent. The use of chemically induced male sterility affects fertility in the plants only for the growing season in which the gametocide is applied (see Carlson, Glenn R., U.S. Pat. No. 4,963,904).

A further method for controlling male sterility includes the use of genes conferring male sterility, such as those disclosed in U.S. Pat. Nos. 3,861,709, 3,710,511, 4,654,465, 5,625, 132, and 4,727,219, each of the disclosures of which are specifically incorporated herein by reference in their entirety. Both inducible and non-inducible male sterility genes can increase the efficiency with which hybrids are made, in that they eliminate the need to physically emasculate the corn plant used as a female in a given cross.

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described by Patterson in U.S. Pat. Nos. 3,861,709 and 3,710,511. These and all patents referred to are incorporated by reference. In addition to these methods, U.S. Pat. No. 5,432,068, discloses a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene which confers male fertility to be transcribed.

Other methods of conferring genetic male sterility exist in the art. These methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et. al, EP089/3010153.8 publication no 329, 308 and PCT application PCT/CA90/00037 published as WO 90/08828).

The presence of a male-fertility restorer gene results in the production of a fully fertile $F_1$ hybrid progeny. If no restorer gene is present in the male parent, male-sterile hybrids are obtained. Such hybrids are useful where the vegetative tissue of the corn plant is used, e.g., for silage, but in most cases, the seeds will be deemed the most valuable portion of the crop, so fertility of the hybrids in these crops must be restored. Therefore, one aspect of the present invention concerns inbred corn plant IAA13BM comprising a single gene capable of restoring male fertility in an otherwise male-sterile inbred or hybrid plant. Examples of male-sterility genes and corresponding restorers which could be employed within the inbred of the invention are well known to those of skill in the art of plant breeding and are disclosed in, for example, U.S. Pat. Nos. 5,530,191, 5,689,041, 5,741, 684, and 5,684,242, the disclosures of which are each specifically incorporated herein by reference in their entirety.

VIII. Corn Transformation

With the advent of molecular biological techniques that have allowed the isolation and characterization of genes that encode specific protein products, scientists in the field of plant biology developed a strong interest in engineering the genome of plants to contain and to express foreign genes, or additional, or modified versions of native or endogenous genes (perhaps driven by different promoters) to alter the traits of a plant in a specific manner. Such foreign, additional and/or modified genes are referred to herein collectively as "transgenes." The present invention, in particular embodiments, also relates to transformed versions of the claimed inbred corn line IAA13BM containing one or more transgenes.

Plant transformation involves the construction of an expression vector which will function in plant cells. Such a vector comprises DNA comprising a gene under control of or operatively linked to a regulatory element. The expression vector may contain one or more such operably linked gene/regulatory element combinations. The vector(s) may be in the form of a plasmid, and can be used, alone or in combination with other plasmids, to provide transformed corn plants, using transformation methods as described below to incorporate transgenes into the genetic material of the corn plant(s).

A. Expression Vectors for Corn Transformation/Marker Genes

Expression vectors include at least one genetic marker, operably linked to a regulatory element that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art. One commonly used selectable marker gene for plant transformation is the neomycin phosphotransferase II (nptII) gene, isolated from a bacterial source, which when placed under the control of plant regulatory signals confers resistance to kanamycin. Fraley et al., *Proc. Natl. Acad. Sci.* U.S.A. 80: 4803 (1983). Another commonly used selectable marker gene is the hygromycin phosphotransferase gene which confers resistance to the antibiotic hygromycin. Vanden Elzen et al., *Plant Mol. Biol.* 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.* 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or bromoxynil. Comai et al., *Nature* 317: 741-744 (1985), Gordon-Kamm et al., *Plant Cell* 2: 603-618 (1990) and Stalker et al., *Science* 242: 419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987), Teeri et al., *EMBO J.* 8: 343 (1989), Koncz et al., *Proc. Natl. Acad. Sci.* U.S.A. 84: 131 (1987), De Block et al., *EMBO J.* 3: 1681 (1984). Another approach to the identification of a relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green™, p. 1-4 (1983) and Naleway et al., *J. Cell Biol.* 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

B. Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter is a promoter which is under environmental control or is induced in response to chemical or hormonal stimuli. Examples of environmental conditions that may effect transcription by inducible promoters include anaerobic conditions or the presence of light. Examples of chemicals that induce expression including salicyclic acid and ABA. Tissue-specific, tissue-preferred, cell type specific, and inducible promoters constitute the class of "non-constitutive" promoters. A "constitutive" promoter is a promoter which is active under most environmental conditions and in all cells.

1. Inducible Promoters

An inducible promoter is operably linked to a gene for expression in corn. Optionally, the inducible promoter is operably linked to a nucleotide sequence encoding a signal sequence which is operably linked to a gene for expression in corn. With an inducible promoter the rate of transcription increases in response to an inducing agent. Any inducible promoter can be used in the instant invention. A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone.

2. Constitutive Promoters

A constitutive promoter is operably linked to a gene for expression in corn or the constitutive promoter is operably linked to a nucleotide sequence encoding a signal sequence which is operably linked to a gene for expression in corn. Many different constitutive promoters can be used in the present invention. Exemplary constitutive promoters include, but are not limited to, the promoters from plant viruses such as the 35S promoter from CaMV and the promoters from such genes as rice actin, maize ubiquitin, and corn H3 histone. Also, the ALS promoter, a XbaI/NcoI fragment 5' to the *Brassica napus* ALS3 structural gene (or a nucleotide sequence that has substantial sequence similarity to the XbaI/NcoI fragment) represents a particularly useful constitutive promoter.

3. Tissue-Specific or Tissue-Preferred Promoters

A tissue-specific promoter is operably linked to a gene for expression in corn. Optionally, the tissue-specific promoter is operably linked to a nucleotide sequence encoding a signal sequence which is operably linked to a gene for expression in corn. Plants transformed with a gene of interest operably linked to a tissue-specific promoter produce the protein product of the transgene exclusively, or preferentially, in a specific tissue. Any tissue-specific or tissue-preferred promoter can be utilized in the instant invention. Exemplary tissue-specific or tissue-preferred promoters include, but are not limited to, a seed-preferred promoter such as that from the phaseolin gene; a leaf-specific and light-induced promoter such as that from cab or rubisco; an anther-specific promoter such as that from LAT52; a pollen specific promoter such as that from Zm13 or a microspore-preferred promoter such as that from apg.

C. Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Any signal sequence known in the art is contemplated by the present invention.

D. Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods.

According to a preferred embodiment, the transgenic plant provided for commercial production of foreign protein is corn. In another preferred embodiment, the biomass of interest is seed. For the relatively small number of transgenic plants that show higher levels of expression, a genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to:

1. Genes that Confer Resistance to Pests or Disease and that Encode:

(a) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*).

(b) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998.

(c) A lectin. See, for example, the disclosure by Van Damme et al., Plant Molec. Biol. 24: 25 (1994), who disclose the nucleotide sequences of several *Clivia miniata* mannose-binding lectin genes.

(d) A vitamin-binding protein such as avidin. See PCT application US93/06487 the contents of which are hereby incorporated by. The application teaches the use of avidin and avidin homologues as larvicides against insect pests.

(e) An enzyme inhibitor, for example, a protease inhibitor or an amylase inhibitor. See, for example, Abe et al., J. Biol. Chem. 262: 16793 (1987) (nucleotide sequence of rice cysteine proteinase inhibitor), Huub et al., Plant Molec. Biol. 21: 985 (1993) (nucleotide sequence of cDNA encoding tobacco proteinase inhibitor I), and Sumitani et al., Biosci. Biotech. Biochem. 57: 1243 (1993) (nucleotide sequence of *Streptomyces nitrosporeus* α-amylase inhibitor).

(f) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(g) An insect-specific peptide or neuropeptide which, upon expression, disrupts the physiology of the affected pest. For example, see the disclosures of Regan, J. Biol. Chem. 269: 9 (1994) (expression cloning yields DNA coding for insect diuretic hormone receptor), and Pratt et al., Biochem. Biophys. Res. Comm 163: 1243 (1989) (an allostatin is identified in *Diploptera puntata*). See also U.S. Pat. No. 5,266,317 to Tomalski et al., who disclose genes encoding insect-specific, paralytic neurotoxins.

(h) An insect-specific venom produced in nature by a snake, a wasp, etc. For example, see Pang et al., Gene 116: 165 (1992), for disclosure of heterologous expression in plants of a gene coding for a scorpion insectotoxic peptide.

(i) An enzyme responsible for a hyperaccumulation of a monterpene, a sesquiterpene, a steroid, hydroxamic acid, a phenylpropanoid derivative or another non-protein molecule with insecticidal activity.

(j) An enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene.

(k) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a corn calmodulin cDNA clone.

(1) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(m) A membrane permease, a channel former or a channel blocker. For example, see the disclosure by Jaynes et al., Plant Sci. 89: 43 (1993), of heterologous expression of a cecropin-β lytic peptide analog to render transgenic tobacco plants resistant to *Pseudomonas solanacearum*.

(n) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(o) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(p) A virus-specific antibody. See, for example, Tavladoraki et al, Nature 366: 469 (1993), who show that transgenic plants expressing recombinant antibody genes are protected from virus attack.

(q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonate. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(r) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

2. Genes that Confer Resistance to a Herbicide, for Example:

(a) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241 (1988), and Mild et al., Theor. Appl. Genet. 80: 449 (1990), respectively.

(b) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., Bio/Technology 7: 61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2 and Acc1-S3 genes described by Marshall et al., Theor. Appl. Genet. 83: 435 (1992).

(c) A herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

3. Genes that Confer or Contribute to a Value-Added Trait, Such as:

(a) Modified fatty acid metabolism, for example, by transforming a plant with an antisense gene of stearoyl-ACP desaturase to increase stearic acid content of the plant. See Knultzon et al., Proc. Natl. Acad. Sci. USA 89: 2624 (1992).

(b) Decreased Phytate Content:

(i) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene.

(ii) A gene could be introduced that reduces phytate content. In corn, this, for example, could be accomplished, by cloning and then reintroducing DNA associated with the single allele which is responsible for corn mutants characterized by low levels of phytic acid. See Raboy et al., Maydica 35: 383 (1990).

(iii) Modified carbohydrate composition effected, for example, by transforming plants with a gene coding for an enzyme that alters the branching pattern of starch. See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtillus* levansucrase gene), Pen et al., Bio/Technology 10: 292 (1992) (production of transgenic plants that express *Bacillus licheniformis*

α-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley α-amylase gene), and Fisher et al., Plant Physiol. 102: 1045 (1993) (corn endosperm starch branching enzyme II).

E. Methods for Corn Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, inc., Boca Raton, 1993) pages 89-119.

1. *Agrobacterium*-Mediated Transformation

One method for introducing an expression vector into plants is based on the natural transformation system of *Agrobacterium*. See, for example, Horsch et al., Science 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant. Sci. 10: 1 (1991). Descriptions of *Agrobacterium* vector systems and methods for *Agrobacterium*-mediated gene transfer are provided by Gruber et al., supra, Miki et al., supra, and Moloney et al., Plant Cell Reports 8: 238 (1989). See also, U.S. Pat. No. 5,591,616, issued Jan. 7, 1997.

2. Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., The Plant Journal 6: 271-282 (1994); U.S. Pat. No. 5,591,616, issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm (See e.g., U.S. Pat. No. 5,550,318; U.S. Pat. No. 5,736,369, U.S. Pat. No. 5,538,880; and PCT Publication WO 95/06128). The expression vector is introduced into plant tissues with a biolistic device that accelerates the microprojectiles to speeds of 300 to 600 m/s which is sufficient to penetrate plant cell walls and membranes. Sanford et al, Part. Sci. Technol. 5: 27 (1987), Sanford, J. C., Trends Biotech. 6: 299 (1988), Klein et al., Bio/Technology 6: 559-563 (1988), Sanford, J. C., Physiol Plant 79: 206 (1990), Klein et al., Biotechnology 10: 268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., Bio/Technology 9: 996 (1991). Alternatively, liposome or spheroplast fusion have been used to introduce expression vectors into plants. Deshayes et al., EMBO J., 4: 2731 (1985), Christou et al., Proc Natl. Acad. Sci. U.S.A. 84: 3962 (1987). Direct uptake of DNA into protoplasts using $CaCl_2$ precipitation, polyvinyl alcohol or poly-L-ornithine have also been reported. Hain et al., Mol. Gen. Genet. 199: 161 (1985) and Draper et al., Plant Cell Physiol. 23: 451 (1982). Electroporation of protoplasts and whole cells and tissues have also been described. U.S. Pat. No. 5,384,253 and Donn et al. In Abstracts of VIIth International Congress on Plant Cell and Tissue Culture IAPTC, A2-38, p 53 (1990); D'Halluin et al., Plant Cell 4: 1495-1505 (1992) and Spencer et al., Plant Mol. Biol. 24: 51-61 (1994).

Other methods which have been described for the genetic transformation of corn include, electrotransformation (U.S. Pat. No. 5,371,003) and silicon carbide fiber-mediated transformation (U.S. Pat. No. 5,302,532 and U.S. Pat. No. 5,464,765).

Following transformation of corn target tissues, expression of the above-described selectable marker genes allows for preferential selection of transformed cells, tissues and/or plants, using regeneration and selection methods now well known in the art. For example, transformed corn immature embryos.

The foregoing methods for transformation would typically be used for producing transgenic inbred lines. Transgenic inbred lines could then be crossed, with another (non-transformed or transformed) inbred line, in order to produce a transgenic hybrid corn plant. Alternatively, a genetic trait which has been engineered into a particular corn line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid corn plant containing a foreign gene in its genome into a line or lines which do not contain that gene.

IX. Genetic Complements

In addition to phenotypic observations, a plant can also be described by its genotype. The genotype of a plant can be described through a genetic marker profile which can identify plants of the same variety, a related variety or be used to determine or to validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs), Isozyme Electrophoresis and Isolelectric Focusing. For example, see Berry, Don, et al., "Assessing Probability of Ancestry Using Simple Sequence Repeat Profiles: Applications to Corn Hybrids and Inbreds", Genetics, 2002, 161:813-824, which is incorporated by reference herein in its entirety.

Particular markers used for these purposes are not limited to the set of markers disclosed herewithin, but are envisioned to include any type of genetically stable marker and marker profile which provides a means of distinguishing varieties. In addition to being used for identification of inbred parents, a hybrid produced through the use of IAA13BM or its parents, and identification or verification of the pedigree of progeny plants produced through the use of IAA13BM, the genetic marker profile is also useful in breeding and developing backcross conversions.

Means of performing genetic marker profiles using SSR polymorphisms are well known in the art. SSRs are genetic markers based on polymorphisms in repeated nucleotide sequences, such as microsatellites. The phrase "simple sequence repeats" or "SSR" refers to di-, tri- or tetra-nucleotide repeats within a genome. The repeat region may vary in length between genotypes while the DNA flanking the repeat is conserved such that the primers will work in a plurality of genotypes. A polymorphism between two genotypes represents repeats of different lengths between the two flanking conserved DNA sequences. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR). The PCR® detection is done by the use of two oligonucleotide primers flanking the polymorphic segment of repetitive DNA followed by DNA amplification. This step involves repeated cycles of heat denaturation of the DNA followed by annealing of the primers to their complementary sequences at low temperatures, and extension of the annealed primers with DNA polymerase. Size separation of DNA fragments on agarose or polyacrylamide gels following amplification, comprises the major part of the methodology.

All publications, patents and patent applications mentioned in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in some detail by way of illustration and example for purposes of clarity and understanding. However, it should be appreciated by those having ordinary skill in the art that certain changes and modifications such as single gene modifications and mutations, somoclonal variants, variant individuals selected from large populations of the plants of the instant inbred and the like may be practiced within the scope of the invention, as limited only by the scope of the appended claims, without departing from the true concept, spirit, and scope of the invention.

What is claimed is:

1. Seed of corn inbred line designated IAA13BM, or a part thereof, representative seed of the line having been deposited under ATCC Accession No. PTA-122499.

2. The seed part of claim 1 selected from the group consisting of pericarp, germ and endosperm.

3. The seed of claim 1, further comprising a coating.

4. A substantially homogenous population of corn seeds consisting essentially of the corn seed of claim 1.

5. A method for producing corn seed, comprising:
    (a) planting seed of claim 1;
    (b) growing a plant from the seed under pollinating conditions; and,
    (c) harvesting seed produced by the plants grown in step (b).

6. Corn seed produced by the method of claim 5.

7. The method of claim 5, further comprising pre-treating the seed of corn inbred line designated IAA13BM, representative seed of the line having been deposited under ATCC Accession No. PTA-122499 before performing step (a).

8. The method of claim 5, further comprising treating the growing plants or soil surrounding the growing plants with an agricultural chemical.

9. A corn plant produced by growing the seed of claim 1.

10. A part of the corn plant of claim 9, selected from the group consisting of an intact plant cell, a plant protoplast, an embryo, a pollen, an ovule, a flower, a kernel, a seed, an ear, a cob, a leaf, a husk, a stalk, a root, a root tip, a brace root, a lateral tassel branch, an anther, a tassel, a glume, a tiller and a silk.

11. Pollen of the plant of claim 9.

12. An ovule of the plant of claim 9.

13. A corn plant, or a part thereof, having all the physiological and morphological characteristics of the corn plant of claim 9.

14. A substantially homogenous population comprising a corn plant of claim 9.

15. A method for producing a corn plant, comprising:
    (a) crossing inbred corn plant IAA13BM, representative seed of the line having been deposited under ATCC Accession No. PTA-122499, with another different corn plant to yield progeny corn seed.

16. The method of claim 15, wherein the other, different corn plant is an inbred corn plant.

17. The method of claim 15, further comprising:
    (b) growing the progeny corn seed from step (a) under self-pollinating or sib-pollinating conditions for about 5 to about 7 generations; and
    (c) harvesting resultant seed.

18. The method of claim 15, further comprising selecting plants obtained from growing at least one generation of the progeny corn seed for a desirable trait.

19. A method of introducing a desired trait into corn inbred line IAA13BM, representative seed of the line having been deposited under ATCC Accession No. PTA-122499, comprising:
    (a) crossing IAA13BM plants with plants of another corn line that comprise a desired trait to produce F1 progeny plants;
    (b) selecting F1 progeny plants that have the desired trait;
    (c) crossing selected progeny plants with IAA13BM plants to produce backcross progeny plants;
    (d) selecting for backcross progeny plants that comprise the desired trait and physiological and morphological characteristics of corn inbred line IAA13BM; and,
    (e) performing steps (c) and (d) one or more times in succession to produce the selected or higher backcross progeny plants that comprise the desired trait and all of the physiological and morphological characteristics of corn inbred line IAA13BM listed in Table 1 as determined at the 5% significance level when grown in the same environmental conditions.

20. A method for producing a hybrid corn seed comprising crossing a first inbred parent corn plant with a second inbred parent corn plant and harvesting resultant hybrid corn seed, wherein the first inbred corn plant or the second inbred corn plant is the corn plant of claim 9.

21. A method for producing a hybrid corn seed, the method comprising:
    (a) planting in pollinating proximity a seed of the corn plant of claim 9 and a seed of another, different corn plant;
    (b) cultivating the seeds into plants that bear flowers;
    (c) allowing cross pollination to occur between the cultivated plants; and
    (d) harvesting seeds produced on at least one of the first inbred corn plant or the second inbred corn plant.

22. The method according to claim 21, wherein the IAA13BM corn plant, representative seed of the line having been deposited under ATCC Accession No. PTA-122499 is the male parent.

23. The method according to claim 21, wherein the IAA13BM corn plant, representative seed of the line having been deposited under ATCC Accession No. PTA-122499 is the female parent.

24. A hybrid corn seed produced by the method according to claim 21.

25. A hybrid corn plant produced by growing the hybrid corn seed of claim 24.

* * * * *